(12) United States Patent
Han et al.

(10) Patent No.: US 10,577,400 B2
(45) Date of Patent: Mar. 3, 2020

(54) METHOD OF MANUFACTURING RECOMBINANT LECTIN PROTEIN AND RECOMBINANT LECTIN PROTEIN MANUFACTURED BY USING THE SAME

(71) Applicant: NATIONAL MARINE BIODIVERSITY INSTITUTE OF KOREA, Chungcheongnam-do (KR)

(72) Inventors: Jong Won Han, Gunsan-si (KR); Hyun-Ju Hwang, Gunsan-si (KR); Hancheol Jeon, Gunsan-si (KR); Jin-Woo Han, Gunsan-si (KR)

(73) Assignee: NATIONAL MARINE BIODIVERSITY INSTITUTE OF KOREA, Chungcheongnam-do (KR)

( * ) Notice: Subject to any disclaimer, the term of this patent is extended or adjusted under 35 U.S.C. 154(b) by 0 days.

(21) Appl. No.: 15/965,993

(22) Filed: Apr. 30, 2018

(65) Prior Publication Data
US 2019/0202874 A1 Jul. 4, 2019

(30) Foreign Application Priority Data
Dec. 28, 2017 (KR) ........................ 10-2017-0182346

(51) Int. Cl.
*C07K 14/42* (2006.01)
*C07K 14/405* (2006.01)

(52) U.S. Cl.
CPC ............ *C07K 14/42* (2013.01); *C07K 14/405* (2013.01)

(58) Field of Classification Search
CPC ....................................................... C07K 14/42
See application file for complete search history.

(56) References Cited

PUBLICATIONS

Hwang et al., "Functional expression and characterization of the recombinant N-acetyl-glucosamine/N-acetyl-galactosamine-specific marine algal lectin BPL3", Marine Drugs, 2018, vol. 16, No. 1, pii: E13. (**Pre-Print published on-line Nov. 28, 2017). doi:10.3390/md16010013.*
Nishi et al., "Development of highly stable galectins: Truncation of the linker peptide confers protease-resistance on tandem-repeat type galectins", FEBS Letters, 2005, vol. 579, pp. 2058-2064.*

* cited by examiner

*Primary Examiner* — Suzanne M Noakes
(74) *Attorney, Agent, or Firm* — Revolution IP, PLLC (57) ABSTRACT

Provided is a method of manufacturing a recombinant BPL3 protein comprising: synthesizing a recombinant BPL3 (rBPL3) gene encoding a *Bryopsis plumosa* lectin (BPL3) protein; preparing a tandem repeat rBPL3 gene including a repeating structure of the rBPL3 gene by tandemly binding the rBPL3 genes through spacers; preparing a recombinant plasmid by inserting the tandem repeat rBPL3 gene into an expression vector; and transforming an expression host by the recombinant plasmid. According to the method, it is possible to maximize expression efficiency of the recombinant lectin and enhance the activity of the manufactured recombinant lectin.

5 Claims, 9 Drawing Sheets

Specification includes a Sequence Listing.

METHOD OF MANUFACTURING RECOMBINANT LECTIN PROTEIN AND RECOMBINANT LECTIN PROTEIN MANUFACTURED BY USING THE SAME

CROSS-REFERENCE TO RELATED APPLICATION

This application claims under 35 U.S.C. § 119(a) the benefit of Korean Patent Application No. 10-2017-0182346 filed on Dec. 28, 2017, the entire contents of which are incorporated herein by reference.

BACKGROUND (a) Technical Field

The present invention relates to a technique of manufacturing a recombinant protein and more particularly, to a technique of manufacturing a recombinant lectin protein capable of maximizing expression efficiency and activity.

(b) Background Art

A lectin, a sugar-binding protein, has a high potential value for scientific uses such as a medical field due to a binding property with carbohydrate, but it has been reported that the production of recombinant lectins having activity is limited to some lectins. The reason is that the production efficiency of the recombinant lectin is low, and the expression of the lectin is not substantially performed by a recombination process or the activity is lost in many cases.

Meanwhile, a *Bryopsis plumosa* lectin (BPL3) derived from *bryopsis plumosa* is a lectin having specificity to GlcNAc and GalNAc and has been proposed to be usable as a material for a molecular probe and the like.

However, the production of a recombinant BPL3 protein using the BPL3 as a motif is not yet smoothly performed, and it is determined that the reason is that there is almost no effectiveness in the production due to the low expression efficiency as described above.

SUMMARY OF THE DISCLOSURE

In consideration of the realities and problems of the lectin production field described above, an object of the present invention is to provide a method of manufacturing a recombinant lectin protein capable of significantly improving the expression efficiency and activity of a recombinant lectin, and particularly, to provide a method capable of enhancing expression efficiency of a recombinant BPL3 derived from *bryopsis plumosa*.

Another object of the present invention is to provide a recombinant BPL3 protein manufactured by the aforementioned method.

An exemplary embodiment of the present invention provides a method of manufacturing a recombinant lectin protein comprising: synthesizing unit lectin genes encoding a lectin protein derived from a natural substance; preparing a tandem repeat lectin gene including a repeating structure of the unit lectin genes by binding the unit lectin genes tandemly through spacers; preparing a recombinant plasmid by inserting the tandem repeat lectin gene into an expression vector; and transforming an expression host by the recombinant plasmid.

Another exemplary embodiment of the present invention provides a method of manufacturing a recombinant BPL3 protein comprising: synthesizing a recombinant BPL3 (rBPL3) gene encoding a *Bryopsis plumosa* lectin (BPL3) protein; preparing a tandem repeat rBPL3 gene including a repeating structure of the rBPL3 gene by tandemly binding the rBPL3 genes through spacers; preparing a recombinant plasmid by inserting the tandem repeat rBPL3 gene into an expression vector; and transforming an expression host by the recombinant plasmid.

The recombinant BPL3 gene may have base sequences represented by SEQ ID NO: 1, the expression vector may be a pET28a (+) vector, and the expression host may be BL21 (λDE3).

The tandem repeat rBPL3 gene may include 2 to 10 rBPL3 genes.

Yet another exemplary embodiment of the present invention provides a recombinant BPL3 protein manufactured by the aforementioned method and having β-GlcNAc-Sp and a glycan binding specificity.

According to the manufacturing method of the recombinant lectin protein of the present invention, it is possible to improve the recombination efficiency of lectin derived from natural substances and manufacture a recombinant lectin protein having high activity.

Further, it is possible to remarkably improve the expression efficiency of the recombinant BPL3 protein to the BPL3 protein derived from *bryopsis plumosa*, and further, it is possible to manufacture a recombinant lectin having β-GlcNAc-Sp without reacting with natural BPL3 and a glycan binding specificity.

A recombinant technology of the present invention is applied to recombinant processes of various lectins later, thereby contributing greatly to mass production of lectins.

Meanwhile, since the glycan binding specificity of the lectin obtained may be minutely changed according to the repetition degree of the gene codon having a tandem repeat structure, it will be expected to more diversify and specialize the utilization of the lectin later.

BRIEF DESCRIPTION OF THE DRAWINGS

The above and other features of the present invention will now be described in detail with reference to certain exemplary embodiments thereof illustrated the accompanying drawings which are given hereinbelow by way of illustration only, and thus are not limitative of the present invention, and wherein.

DETAILED DESCRIPTION

Hereinafter, a method of manufacturing a recombinant lectin protein of the present invention will be described in detail. However, the following descriptions are illustrative for helping the understanding of the present invention, and the technical spirit of the present invention is not limited to the following descriptions. The technical spirit of the present invention may be interpreted or limited only by appended claims to be described below.

In order to manufacture a recombinant lectin protein of the present invention, first, unit lectin genes encoding a lectin protein derived from a natural substance to be recombined needs to be synthesized.

A gene sequence of the lectin derived from the natural substance may be easily obtained by a known DB or the like. Using the obtained sequence, base sequences are designed and synthesized according to an expression host to be applied. The 'unit lectin gene' refers to an optimized gene codon synthesized above. The unit lectin gene may be synthesized by copying a sequence structure of a natural lectin having a repeated sequence. However, the remaining base sequence except for the copying region is modified and designed to be different from the sequence of the natural lectin in order to maximize the applied host and the expression efficiency.

The prepared unit lectin genes are not used as they are, but are subjected to repetitive structuring processes. That is, the unit lectin genes are tandemly bound to each other through spacers to prepare a tandem repeat lectin gene including the repeating structure of the unit lectin genes. The spacer is a short base sequence that tandemly binds the unit lectin genes, and the binding between the repeated genes may be variously performed by employing a known gene manipulation technique.

The tandem repeat lectin gene includes at least two repeat regions, that is, two or more unit lectin genes, and the repetition degree or the repetition number may be determined in consideration of various variables, such as application fields of the recombinant lectin and a gene sequence of the lectin derived from the natural substance. However, if the repetition number is too large, compatibility with an expression vector may be deteriorated, and thus, repeating of 10 times or more is not preferable.

Next, a recombinant plasmid is prepared by inserting the tandem repeat lectin gene into an expression vector. Since a type of expression vector is a variable that can affect the expression efficiency of the lectin, the expression vector needs to be carefully selected by considering various factors such as the application fields of the lectin and characteristics of the lectin derived from the natural substance as described above in addition to the type of expression host.

Finally, the recombinant lectin protein may be expressed through a transformation process by applying the recombinant plasmid to the expression host. As the expression host, bacteria and the like are used, and a type of expression host has an organic relation with the design and the synthesis process of the unit lectin genes.

Compared with the production method using only the unit lectin genes, in the case of using the gene subjected to the repetitive structuring process, the expression efficiency is remarkably exhibited and the expression efficiency is increased exponentially. In addition, the lectin prepared using the repeating structural gene may exhibit a minute characteristic change as compared with the lectin derived from the natural substance, and thus various studies for systematizing the causality between the repeating structure and the lectin characteristic will be promoted later.

Hereinafter, as an exemplary embodiment of the present invention, a method of manufacturing a recombinant lectin (rBPL3) protein using *Bryopsis plumosa* lectin (BPL3) derived from *bryopsis plumosa* as a motif will be described in detail through detailed Examples, experiments, and the like. Meanwhile, the technical spirit of the present invention is not restricted or limited from the following detailed descriptions. In addition, the following descriptions may be made with reference to the accompanying drawings.

EXAMPLE

Preparation of Vector for Producing Recombinant Protein

A gene sequence of *Bryopsis plumosa* lectin 3 (BPL3) was obtained from NCBI DB (ACC. KX867966). The gene sequence was optimized with gene codons of the bacteria using a Geneious program. The BPL3 gene was synthesized by copying a sequence structure of lectin having a repeated sequence. The BPL3 gene was cloned into an expression vector pET28a (+) and transformed into an expression host BL21 (λDE3). Transformants were selected from an LB medium containing 25 μg/mL of kanamycin.

Figure 1:
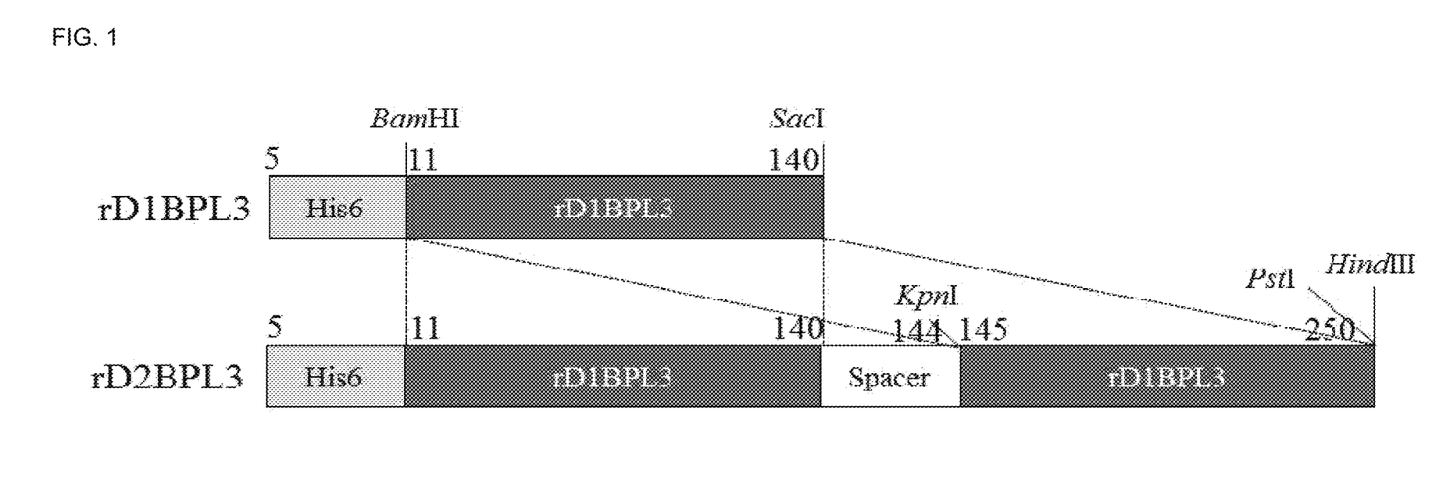
FIG. 1 is a schematic diagram for comparing a single structure and a repeating structure of a recombinant lectin gene.

FIG. 1 is a schematic diagram for comparing a single structure and a repeating structure of a recombinant lectin gene. Referring to FIG. 1, a recombinant lectin (rD2BPL3) gene having a repeating structure was prepared by binding unit recombinant lectin (rD1BPL3) genes by spacers, and restrictive enzyme sites were inserted into the ends of the single structure and the repeating structure to discriminate each structure.

Figure 2:
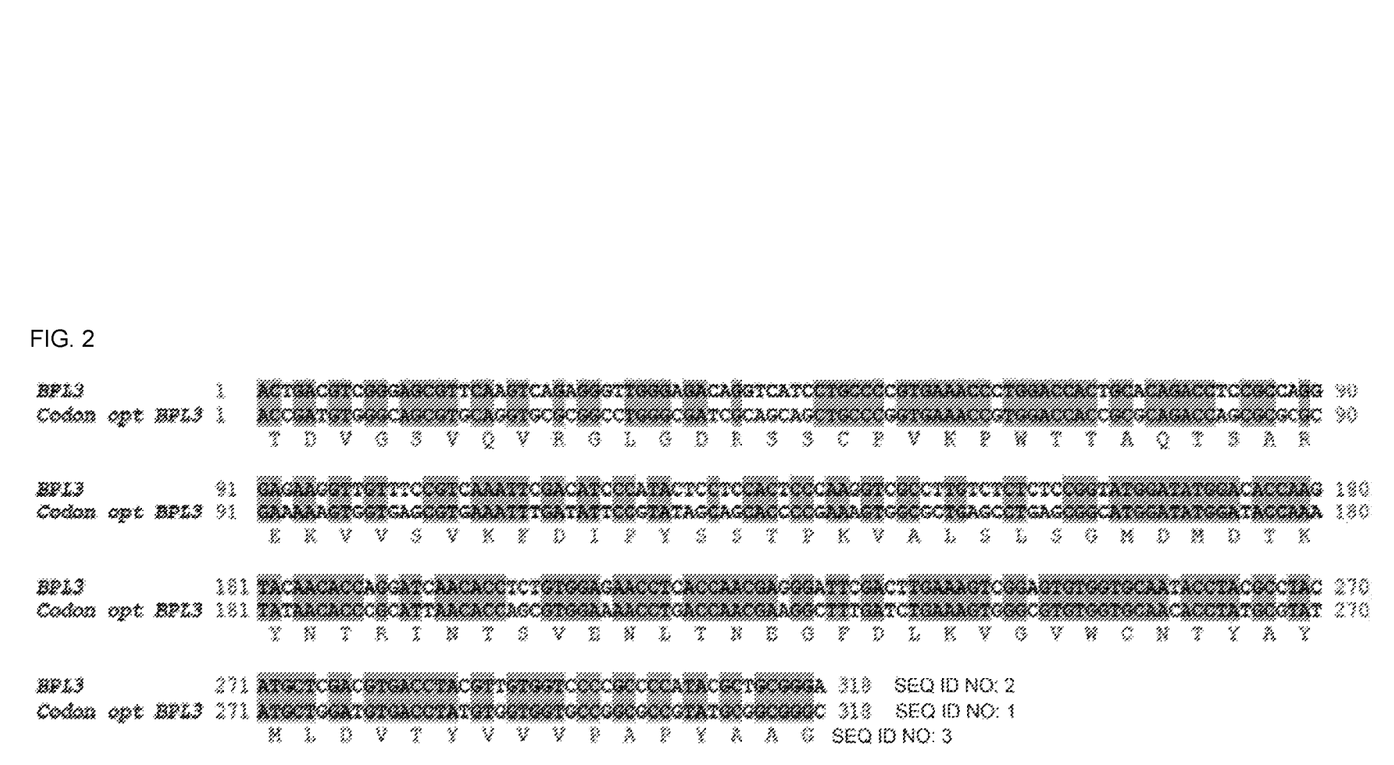
FIG. 2 is a comparison diagram of a *bryopsis plumosa*-derived BPL3 gene having SEQ ID NO: 2, an optimized recombinant BPL3 gene sequence having SEQ ID NO: 1, and a recombinant BPL3 protein having SEQ ID NO: 3.

FIG. 2 is a comparison diagram of a *bryopsis plumosa*-derived BPL3 gene and an optimized recombinant BPL3 gene sequence. Referring to FIG. 2, the optimized recombinant BPL3 gene includes a region that repeatedly overlaps with a BPL3 gene derived from the *bryopsis plumosa*, and base sequences of some spaced sections were modified and designed. On the other hand, base sequences of the optimized recombinant BPL3 gene was represented by SEQ ID NO: 1.

Optimization of Expression of Recombinant Protein

Optimal conditions for expression of recombinant proteins were determined by measuring expression rates according to expression temperatures (20, 25, 30, and 37° C.), culture times (1, 3, 5, and 7 hours) and IPTG concentrations (0.1, 0.2, 0.5 and 1 mM), respectively. Protein expression was induced by adding IPTG at a concentration of bacteria of OD 0.4 to 0.6. The total protein for measuring the protein expression rate was added with a 1×SDS sample buffer to be 0.2 mL/mL culture and then heated at 90° C. for 5 minutes to be obtained. Protein extracts were centrifuged at 20,000 g for 5 minutes to remove insoluble residues and subjected to SDS-PAGE.

Overexpression and Purification of Recombinant BPL3

A bacterial culture solution (500 mL) was centrifuged at 5,000 g for 10 minutes, and the precipitate was dissolved using 50 mL of Urea extraction buffer (50 mM NaH2PO4, 300 mM NaCl, 8 M Urea, pH 8.0). Bacteria were ruptured using a sonicator (22% amplitude, 5 sec/3 sec (On/Off), 20 minutes) and centrifuged to obtain a supernatant. The rBPL3 was purified from bacterial fractions using an NGC chromatography system (BIO-RAD) and 1 mL Ni-NTA affinity chromatography. The bound rBPL3 was eluted sequentially using 75 mM, 125 mM, and 250 mM of imidazoles. The purify of the eluted fractions was confirmed using SDS-PAGE, and the fractions containing the rBPL3 was collected by one tube.

[Experiment and Evaluation]

Hereinafter, for convenience, the recombinant lectin obtained by the gene having the single structure is referred to as 'rD1BPL3', and the recombinant lectin obtained by the gene having the repeating structure is referred to as 'rD2BPL3'. In addition, BPL3 derived from *bryopsis plumosa* is referred to as Native BPL3 as a comparative target.

Evaluation of Expression Rate

Figure 3:
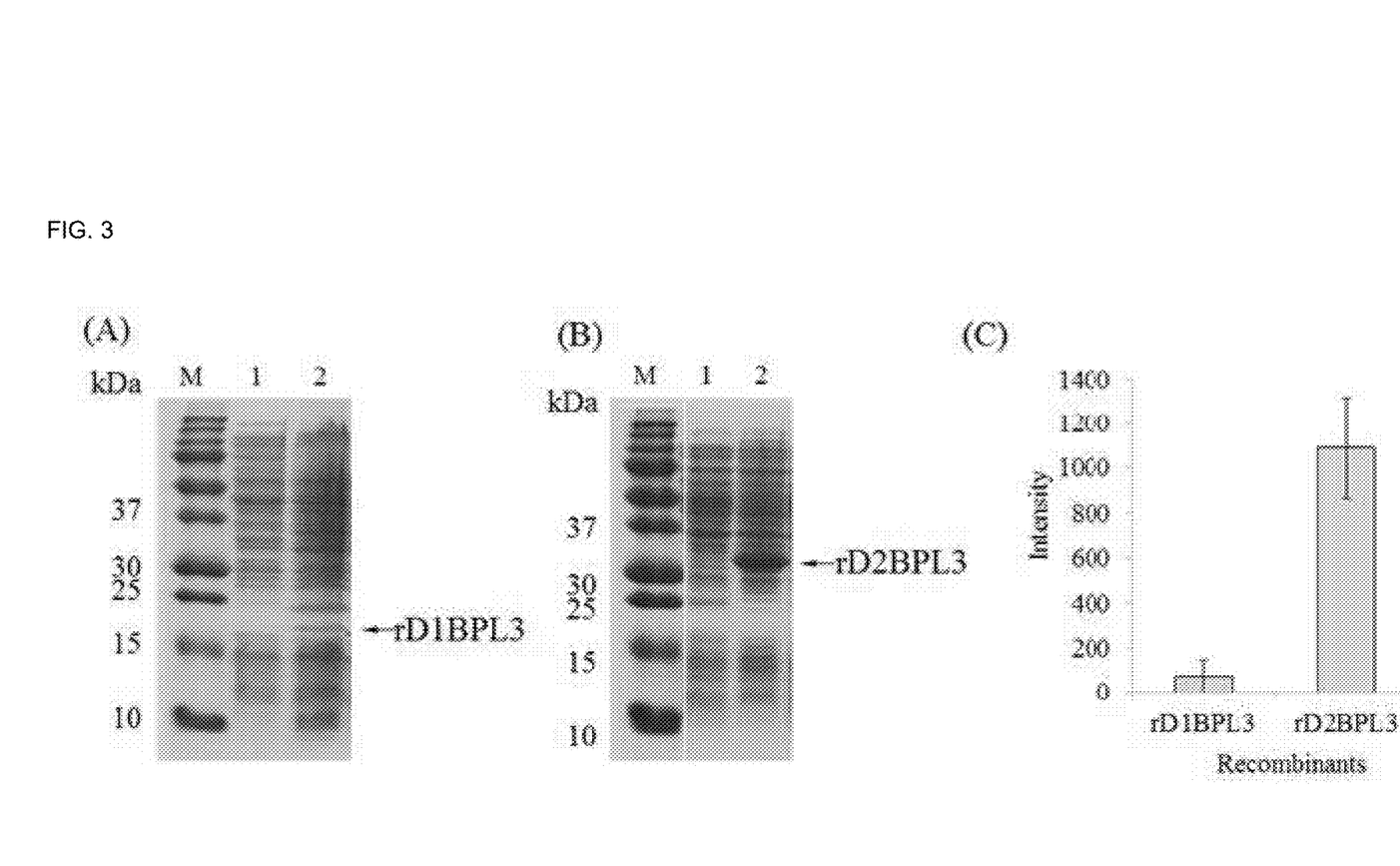
FIG. 3 is a diagram illustrating results of evaluating expression characteristics of a lectin (rD2BPL3) expressed by the repeating structure and a lectin (rD1BPL3) expressed by the single structure.

FIG. 3 is a diagram illustrating results of evaluating expression characteristics of a lectin (rD2BPL3) expressed by the repeating structure and a lectin (rD1BPL3) expressed by the single structure.

After induction by IPTG, a difference in expression rate between the repeating structure (rD2BPL3) and the single structure (rD1BPL3) was confirmed. BPL3s having the single structure and the repeating structure all were successfully expressed in bacteria. The rD2BPL3 had 10 times higher expression rate than the rD1 BPL3.

Referring to FIG. 3, as a result of an optimizing experiment for producing rBPL3 in transformed *E. coli* BL21 (DE3), the expression rate of the rBPL3 was high at the rD2BPL3 as compared with the rD1BPL3.

In FIG. 3, details of (A), (B) and (C) are as follows.

A: rD1 BPL3 SDS-PAGE result. M; marker, Lane 1; uninduced protein, Lane 2; induced protein B: rD2BPL3 SDS-PAGE result. M; marker, Lane 1; uninduced protein, Lane 2; induced protein (0.4 mM IPTG)

C: result of comparing expression amounts of rD1 BPL3 and rD2BPL3

Evaluation of Expression Rate for Each IPTG Concentration

Figure 4:
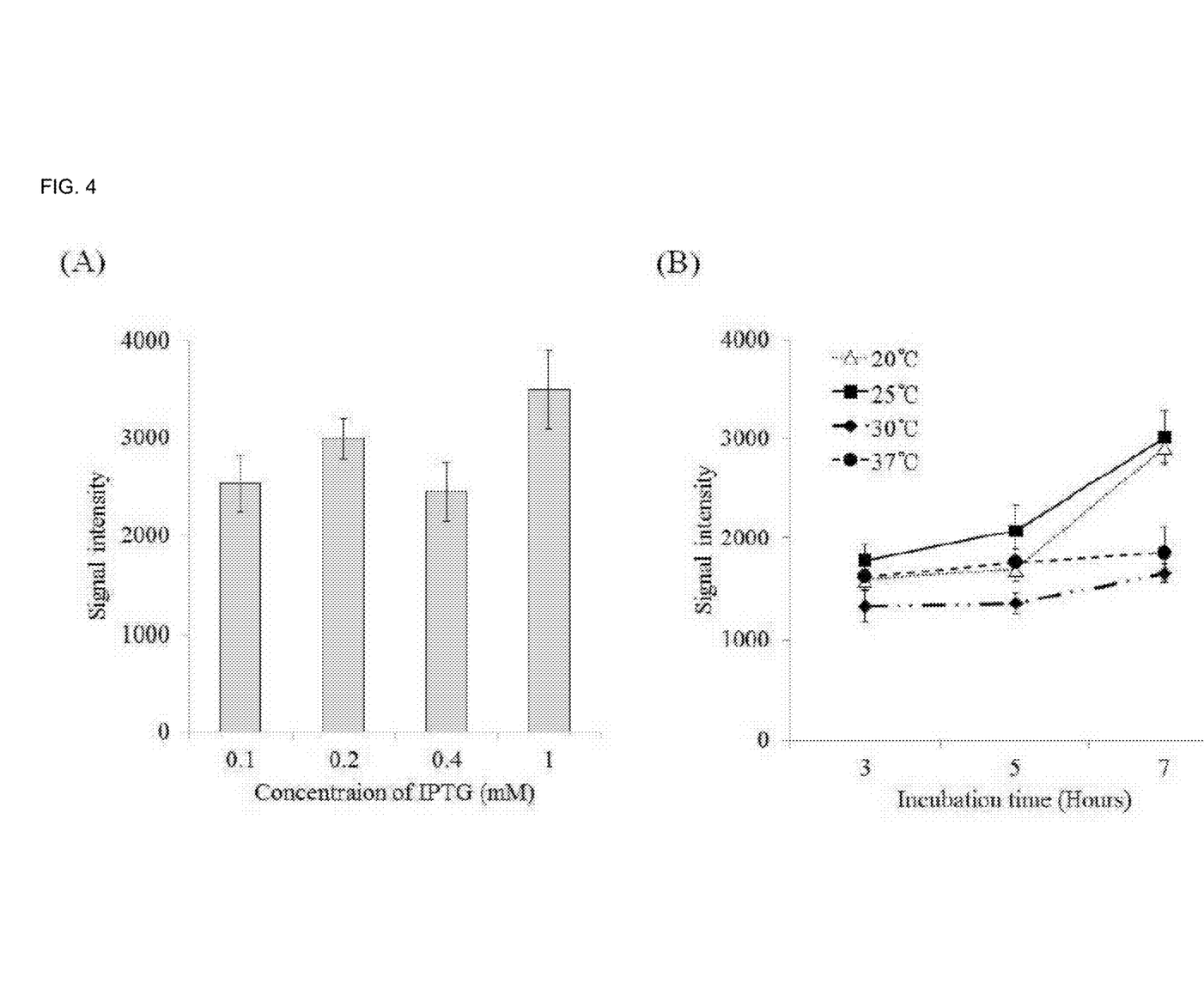
FIG. 4 is a graph for comparing expression rates of the rD2BPL3 for each IPTG concentration and for each time.

FIG. 4 is a graph of comparing expression rates of rD2BPL3 for each IPTG concentration and for each time. Referring to FIG. 3, in order to determine optimal expression conditions of the rD2BPL3, an expression rate for each IPTG concentration and an expression rate according to the time were compared. The highest expression rate was shown at 1 mM of IPTG concentration, and the culture time did not affect the protein expression.

In FIG. 4, details of (A) and (B) are as follows.

A: Expression rate according to IPTG concentration. M; marker, Lane 1; uninduced protein, Lane 2-5; induced protein (IPTG 0.1 mM, 0.2 mM, 0.5 mM, 1 mM)

B: rD2BPL3 expression rate according to time and temperature (0.4 mM IPTG; 1, 3, 5, 7(h))

Ni-NTA Affinity Chromatography

Figure 5:
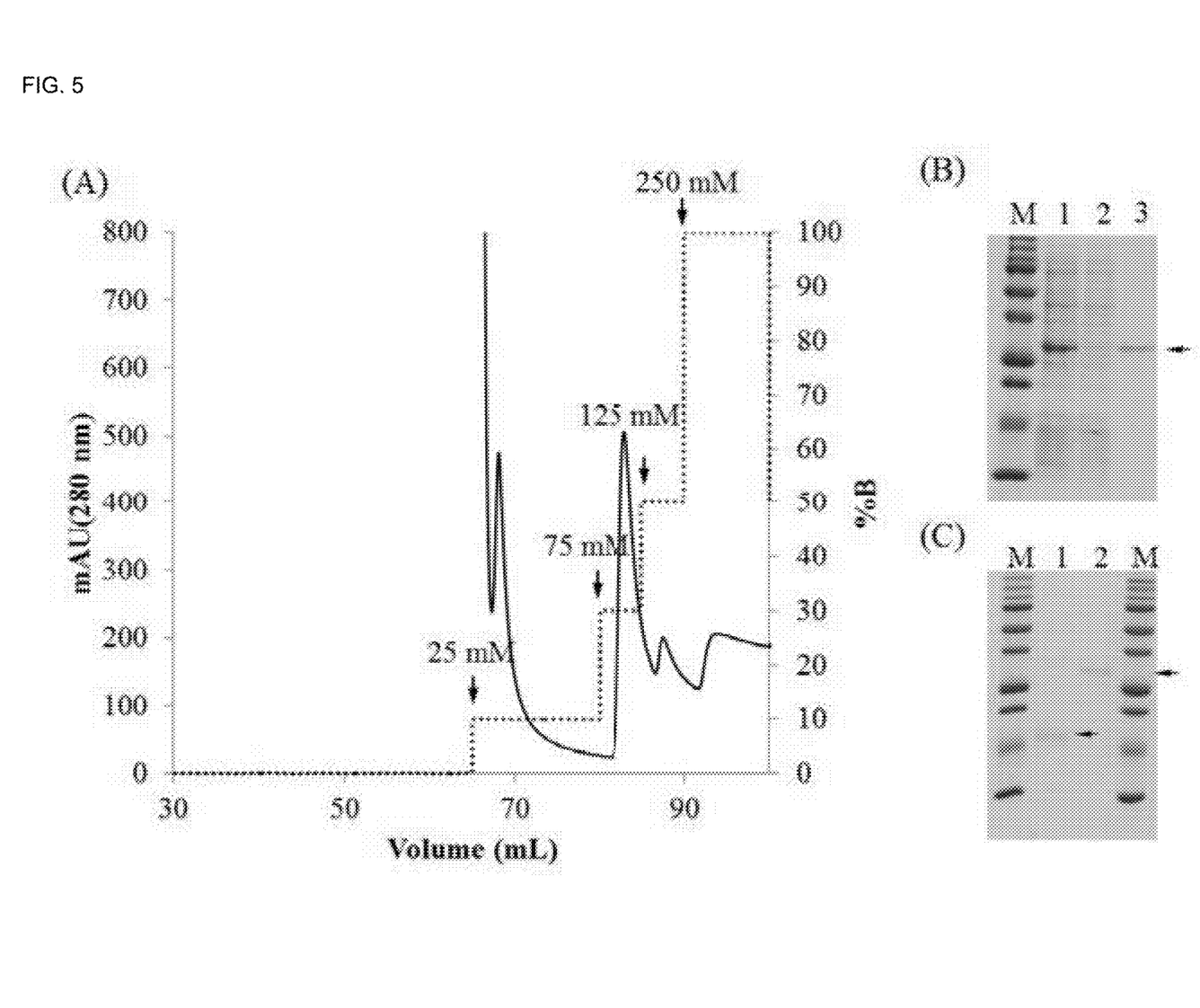
FIG. 5 is a diagram for confirming a purification result of rBPL3 through Ni-NTA affinity chromatography.

FIG. 5 is a diagram of confirming a purification result of rBPL3 through Ni-NTA affinity chromatography.

Referring to FIG. 5, BPL3 was purified purely from a bacterial culture solution using Ni-NTA affinity chromatography. Most of the rD2BPL3 was isolated from a column at 75 mM of imidazole.

In FIG. 5, details of (A), (B) and (C) are as follows.

A: Chromatographic purification

B: M; maker, Lane 1; crude protein, Lane 2; flow-through, Lane3; elution (75 mM Imidazole)

C: Purified recombinant lectins; M, Molecular weight marker; lane 1; rD1BPL3, lane 2; rD2BPL3

Establishment of Refolding Conditions

Figure 6:
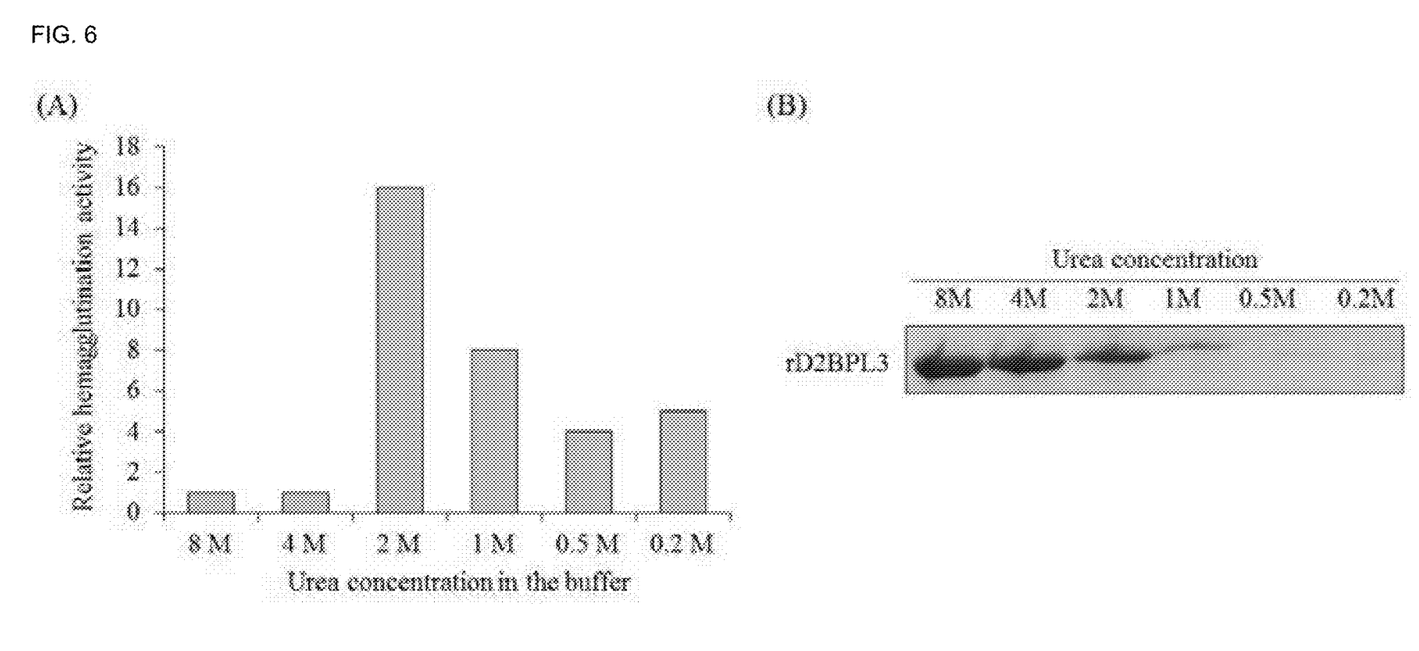
FIG. 6 is a diagram illustrating an activity change and a SDS-PAGE result according to a urea concentration.

FIG. 6 is a diagram illustrating an activity change and a SDS-PAGE result according to a urea concentration. Referring to FIG. 6, denaturated rD2BPL3 was refolded using a instantaneous dilution method. When the protein was diluted to 2M Urea or less, most of the protein was insolubilized and the recovery rate was less than 10%. The protein recovery rate was about 50% under about 2M Urea. As the result of measuring a change in activity according to a concentration, the highest activity was shown at the 2M Urea.

Evaluation of Hemagglutination Activity and Sugar-binding Property of rD2BPL3

Figure 7:
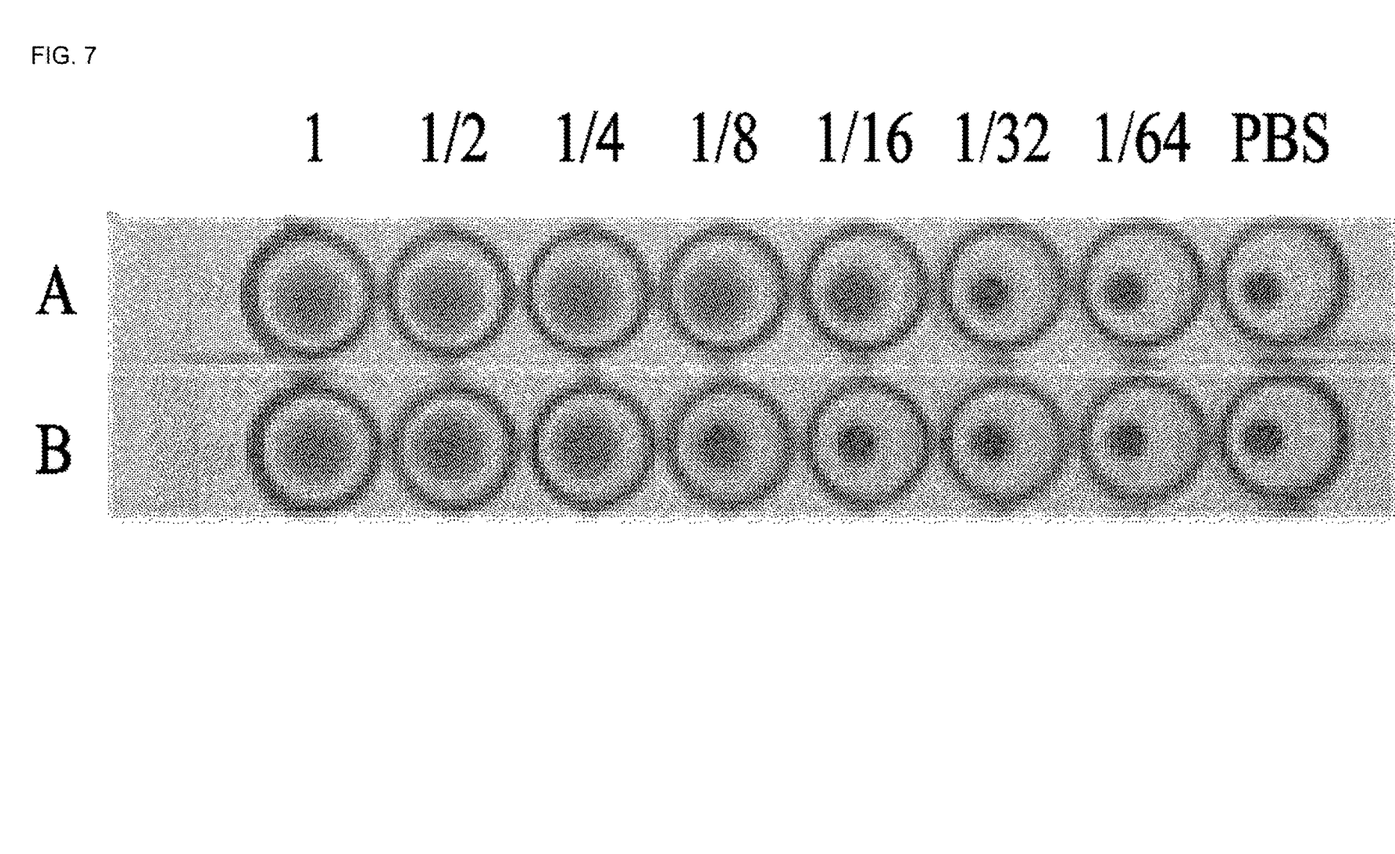
FIG. 7 is a photograph for confirming hemagglutination activity of refolded rBPL3 in types A and B.

The hemagglutination activity of rD2BPL3 was measured. The purified rD2BPL3 coagulated blood cells of types A and B and strongly reacted with the A type blood cell. FIG. 7 is a photograph for confirming hemagglutination activity of refolded rBPL3 in types A and B. This result is the same result as the hemagglutination characteristic of existing Native BPL3.

Figure 8:
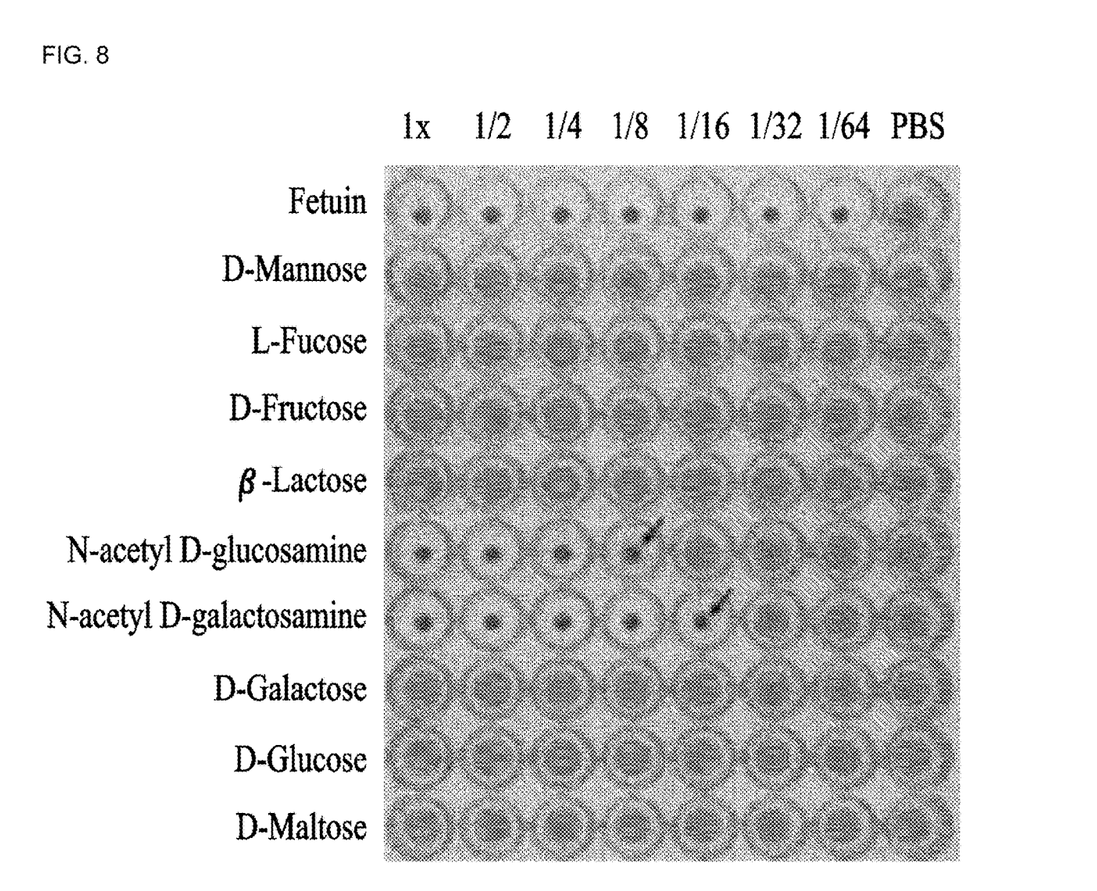
FIG. 8 is a photograph showing that the activity of the refolded rBPL3 is inhibited by N-acetyl D-glucosamine and N-acetyl D-glactosamine.

FIG. 8 is a photograph showing that the activity of the refolded rBPL3 is inhibited by N-acetyl D-glucosamine and N-acetyl D-glactosamine. Referring to FIG. 8, experiments on inhibition of hemagglutination activity for 10 kinds of sugars including GlcNAc and GalNAc which inhibited hemagglutination activity of Native BPL3 were conducted. The hemagglutination activity of rBPL3 was inhibited by GlcNAc (125 mM) and GalNAc (62.5 mM) the same as the native BPL3 identified in Han et al., 2010.

Table 1 below shows results of confirming that the Native BPL3 and the rD2BPL3 inhibit the hemagglutination activity by the same sugar.

TABLE 1

| | Minimum inhibitory concentration | |
|---|---|---|
| Substance | Native BPL3 | rD2BPL3 |
| Fetuin | 19.53§ | 4.88§ |
| d-Mannose | NI | NI |
| 1-Fucose | NI | NI |
| d-Fructose | NI | NI |
| β-Lactose | NI | NI |
| N-acetyl-d-glucosamine | 125 | 62.5 |
| N-acetyl-d-galactosamine | 62.5 | 31.25 |
| d-Galactose | NI | NI |
| d-Glucose | NI | NI |
| d-Maltose | NI | NI |

§concentration, µg/mL,
NI, the absence of inhibition at 500 mM.

Measurement of Glycan Binding Specificity

Affinity with glycans was measured using RayBio® Glycan Array 100. The rBPL3 and the Native BPL3 were conjugated with biotin and then dialyzed to remove unreacted biotin.

Figure 9:
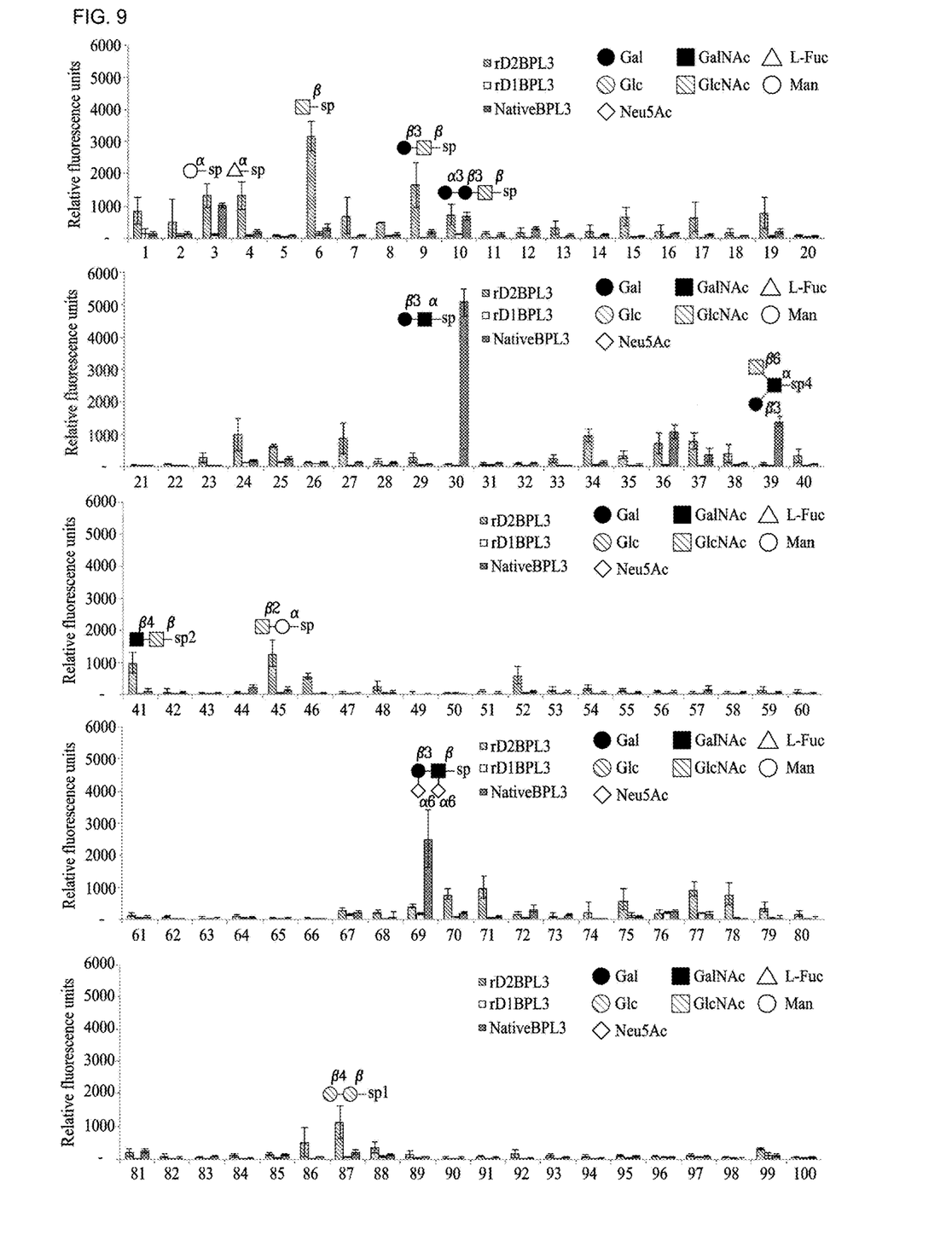
FIG. 9 is a graph for comparing glycan binding specificities of Native BPL3, rD1BPL3, and rD2BPL3.

FIG. 9 is a graph for comparing glycan binding specificities of Native BPL3, rD1BPL3, and rD2BPL3. Referring to FIG. 9, the Native BPL3 reacted with 5 glycans of 100 glycans and observed a strong signal for a glycan of Gal-β-1,3-GalNAc-α-Sp. The rD2BPL3 reacted with 8 glycans of 100 glycans and observed a strong signal for a glycan of β-GlcNAc-Sp. The rD1BPL3 did not observe a strong signal in 100 glycans.

The glycan array result showed that the Native BPL3 and the rD2BPL3 were specifically bound to different sugars except for α-Man-Sp and Gal-α-1,3-Gal-β-1,3-GlcNAc-β-Sp. In a coagulation inhibition experiment, both the Native BPL3 and the rD2BPL3 were not inhibited by α-Man, but as the glycan array result, both proteins were specifically bound to α-Man-Sp. In the coagulation inhibition experiment, there is a possibility that the coagulation is not inhibited by α-Man because a competitive reaction with more complex glycans using the blood cells occurs. α-Manspecific sugar-binding proteins are recognized as viral inhibitors and additional studies are required.

There is a difference in that the rD2BPL3 specifically binds to β-GlcNAc-Sp and the Native BPL3 does not react with β-GlcNAc-Sp. On the other hand, the Native BPL3 showed a stronger binding force to Gal-β-1,3-GalNAc-α-Sp. In addition, Gal-α-1,3-Gal-β-1,3-GlcNAc-β-Sp showed affinity with the two proteins. Therefore, it is determined that the Native BPL3 has higher affinity with the a-structure and the rBPL3 has higher affinity with the β-structure.

A Gal/GalNAc binding protein has been proposed as a candidate substance for amoebidase vaccine, and β-D-Glc-NAc-D-GalNAc having the specificity of the rD2BPL3 has been proposed as a cancer biomarker and conduction of subsequent studies is required.

What is claimed is:

1. A method of manufacturing a recombinant BPL3 protein comprising:
synthesizing a recombinant *Bryopsis plumosa* lectin (rBPL3) gene encoding a *Bryopsis plumosa* lectin (BPL3) protein;

preparing a tandem repeat rBPL3 gene including a repeating structure of the rBPL3 gene by tandemly binding the rBPL3 genes through spacers;

preparing a recombinant plasmid by inserting the tandem repeat rBPL3 gene into an expression vector; and transforming an expression host with the recombinant plasmid.

2. The method of claim 1, wherein the recombinant BPL3 gene comprises SEQ ID NO: 1.

3. The method of claim 1, wherein the expression vector is a pET28a (+) vector.

4. The method of claim 1, wherein the expression host is BL21 (λDE3).

5. The method of claim 1, wherein the tandem repeat rBPL3 gene includes 2 to 10 rBPL3 genes.

* * * * *

SEQUENCE LISTING

```
<160> NUMBER OF SEQ ID NOS: 3

<210> SEQ ID NO 1
<211> LENGTH: 318
<212> TYPE: DNA
<213> ORGANISM: Artificial Sequence
<220> FEATURE:
<223> OTHER INFORMATION: rBPL3 Nucleotide Codon Optimized

<400> SEQUENCE: 1
accgatgtgg gcagcgtgca ggtgcgcggc ctgggcgatc gcagcagctg cccggtgaaa      60
ccgtggacca ccgcgcagac cagcgcgcgc gaaaaagtgg tgagcgtgaa atttgatatt     120
ccgtatagca gcaccccgaa agtggcgctg agcctgagcg gcatggatat ggataccaaa     180
tataacaccc gcattaacac cagcgtggaa aacctgacca acgaaggctt tgatctgaaa     240
gtgggcgtgt ggtgcaacac ctatgcgtat atgctggatg tgacctatgt ggtggtgccg     300
gcgccgtatg cggcgggc                                                   318

<210> SEQ ID NO 2
<211> LENGTH: 318
<212> TYPE: DNA
<213> ORGANISM: Artificial Sequence
<220> FEATURE:
<223> OTHER INFORMATION: bryopsis plumose-derived BPL3 gene

<400> SEQUENCE: 2
actgacgtcg ggagcgttca agtcagaggg ttgggagaca ggtcatcctg ccccgtgaaa      60
ccctggacca ctgcacagac ctccgccagg gagaaggttg tttccgtcaa attcgacatc     120
ccatactcct ccactcccaa ggtcgccttg tctctctccg gtatggatat ggacaccaag     180
tacaacacca ggatcaacac ctctgtggag aacctcacca cgagggatt cgacttgaaa      240 gtcggagtgt ggtgcaatac ctacgcctac atgctcgacg tgacctacgt tgtggtcccc     300
gccccatacg ctgcggga                                                   318

<210> SEQ ID NO 3
<211> LENGTH: 106
<212> TYPE: PRT
<213> ORGANISM: Artificial Sequence
<220> FEATURE:
<223> OTHER INFORMATION: recombinant BPL3 protein

<400> SEQUENCE: 3

Thr Asp Val Gly Ser Val Gln Val Arg Gly Leu Gly Asp Arg Ser Ser
1               5                   10                  15

Cys Pro Val Lys Pro Trp Thr Thr Ala Gln Thr Ser Ala Arg Glu Lys
            20                  25                  30

Val Val Ser Val Lys Phe Asp Ile Pro Tyr Ser Ser Thr Pro Lys Val
        35                  40                  45

Ala Leu Ser Leu Ser Gly Met Asp Met Asp Thr Lys Tyr Asn Thr Arg
    50                  55                  60
```

```
Ile Asn Thr Ser Val Glu Asn Leu Thr Asn Glu Gly Phe Asp Leu Lys
65                  70                  75                  80

Val Gly Val Trp Cys Asn Thr Tyr Ala Tyr Met Leu Asp Val Thr Tyr
                85                  90                  95

Val Val Val Pro Ala Pro Tyr Ala Ala Gly
            100             105
```